United States Patent [19]
Grandone et al.

[11] Patent Number: 5,294,404
[45] Date of Patent: Mar. 15, 1994

[54] REAGENT PACK FOR IMMUNOASSAYS

[75] Inventors: Cass J. Grandone, Lake Forest; Gary L. Zuck, Prospect Heights; Stephen L. Herchenbach, Grayslake; James T. Tyranski, Oakwood Hills; Robert J. Nelson, Highland Park, all of Ill.

[73] Assignee: Abbott Laboratories, Abbott Park, Ill.

[21] Appl. No.: 999,178

[22] Filed: Dec. 29, 1992

Related U.S. Application Data

[63] Continuation of Ser. No. 709,726, Jun. 3, 1991, abandoned.

[51] Int. Cl.$^5$ ............................................. G01N 35/00
[52] U.S. Cl. ........................................ 422/64; 422/63; 422/104; 422/102; 436/43; 436/45; 436/47
[58] Field of Search ............... 422/62, 64, 65, 67, 422/68.1, 102, 104, 63; 435/287, 312, 809; 436/43, 45, 47

[56] References Cited

U.S. PATENT DOCUMENTS

| | | | |
|---|---|---|---|
| 4,287,154 | 9/1981 | Sommer | 422/64 |
| 4,287,155 | 9/1981 | Tersteeg et al. | 422/64 |
| 4,322,216 | 3/1982 | Lillig et al. | 422/64 X |
| 4,795,710 | 1/1989 | Muszak et al. | 435/287 |
| 4,855,110 | 8/1989 | Marker et al. | 422/102 |
| 4,956,148 | 9/1990 | Grandone | 422/64 |
| 5,075,802 | 12/1991 | Fechtner | 422/102 |
| 5,077,013 | 12/1991 | Guigan | 422/64 |

FOREIGN PATENT DOCUMENTS

| | | |
|---|---|---|
| 0287900 | 4/1988 | European Pat. Off. |
| 0353591 | 7/1989 | European Pat. Off. |
| 0353592 | 7/1989 | European Pat. Off. |
| 0355849 | 8/1989 | European Pat. Off. |

OTHER PUBLICATIONS

Chemical Chemistry, vol. 34, No. 9, Sep. 1988, Winston US pp. 1726-1732; "The Abbott IMx(TM) Automated Benchtop Immunochemistry Analyzer System".

"The Abbott IMx® Automated Benchtop Immunochemistry Analyzer System", M. Fiore et al., Clinical Chemistry, vol. 23, No. 9, 1988.

Abbott Document #1.

"The Abbott IMX® and IMx Select TM Systems" C. H. Keller et al., Journal of Clinical Immunoassay, vol. 14, No. 2, Summer 1991.

Primary Examiner—James C. Housel
Assistant Examiner—Long V. Le
Attorney, Agent, or Firm—Richard D. Schmidt

[57] ABSTRACT

A reagent pack for carrying a plurality of individual reagent containers which are required for performing a specific immunoassay is suitable both for transportation of the assays from the manufacturer to the instrumentation site and for use at the instrumentation site during the running of the specific immunoassays on an assay specimen.

5 Claims, 9 Drawing Sheets

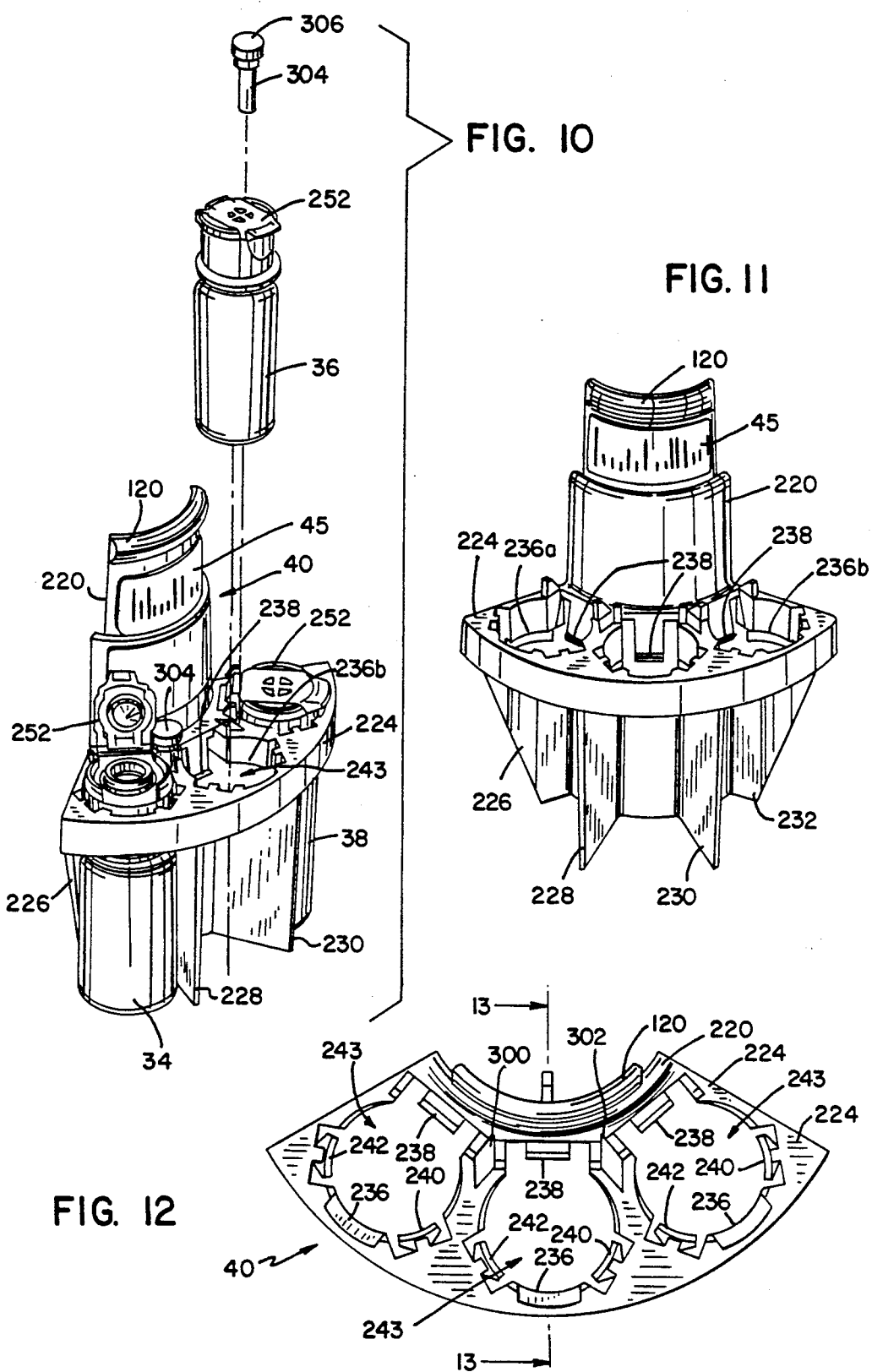

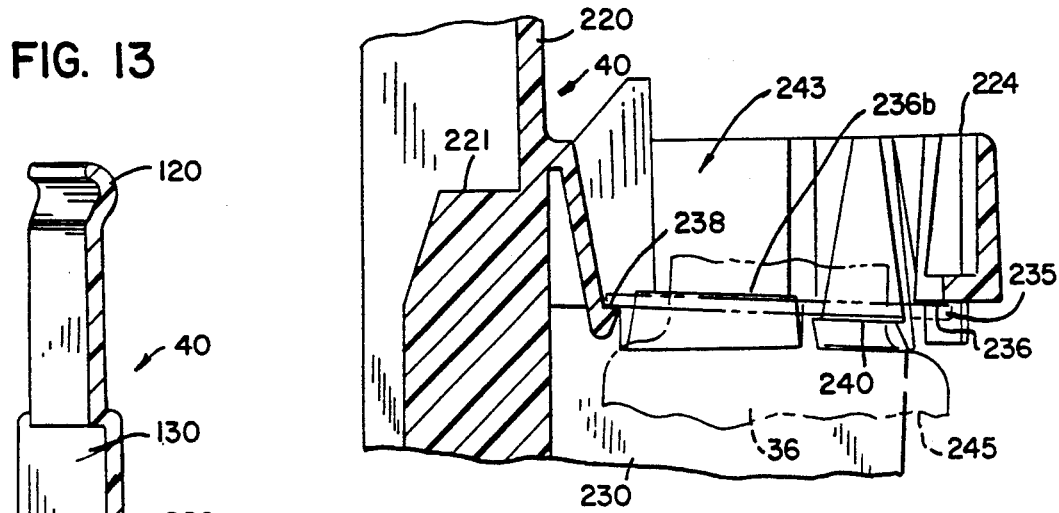
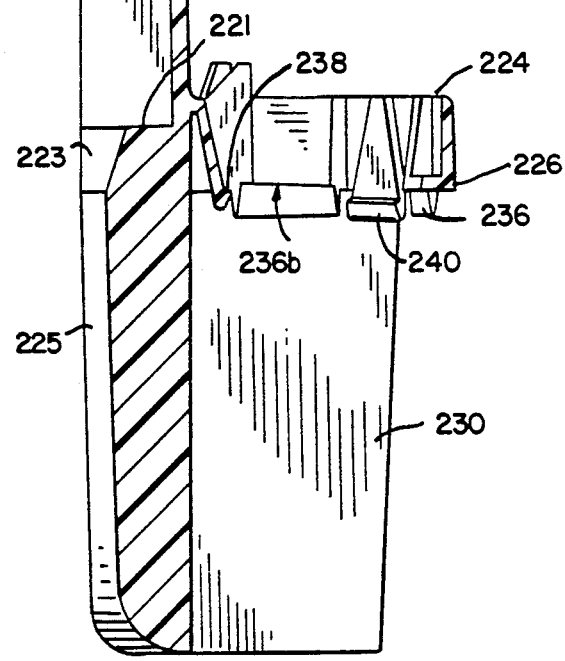
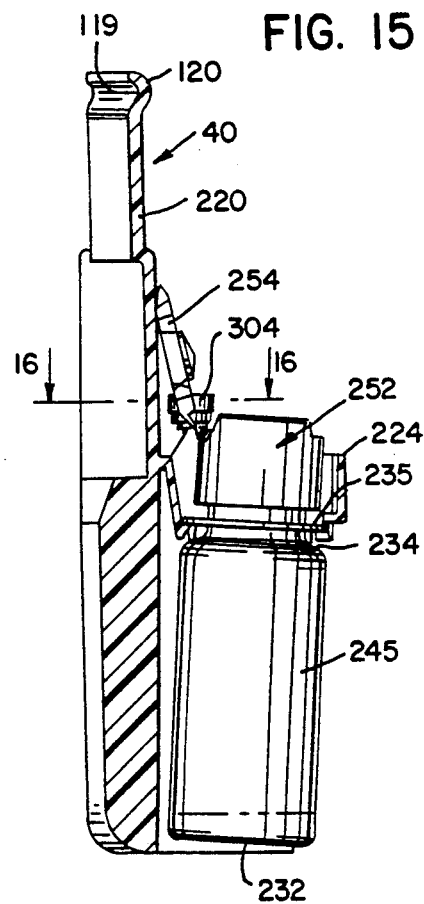
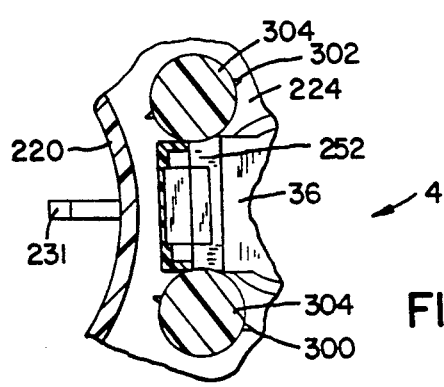

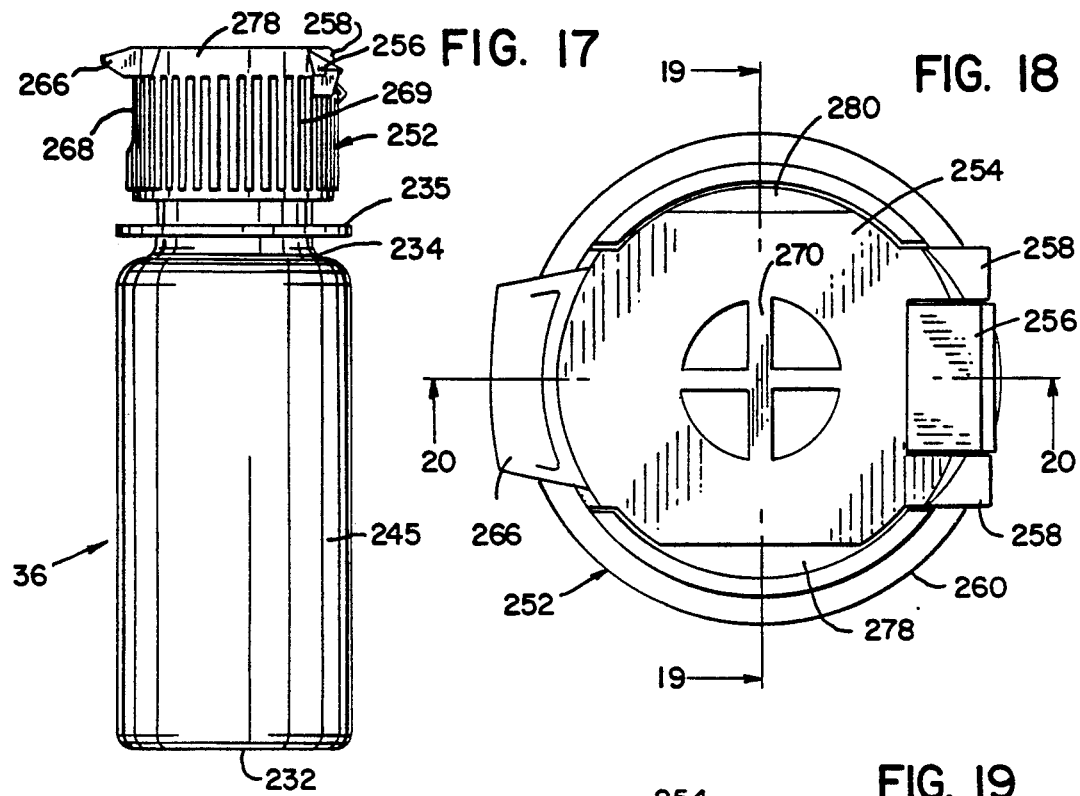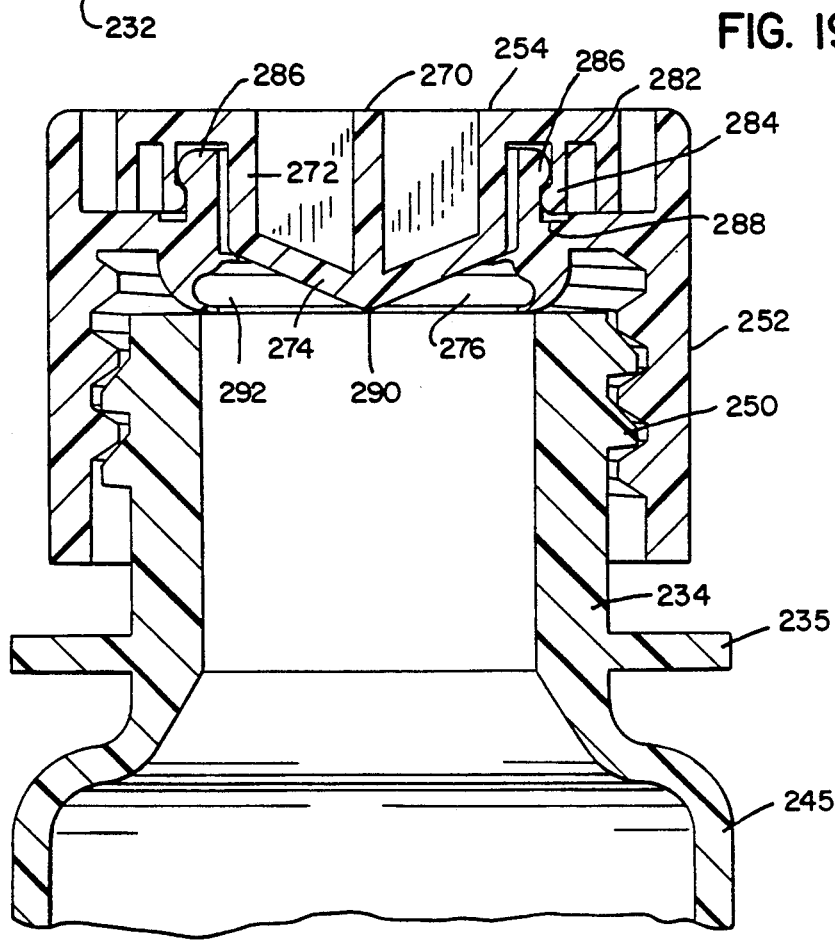

REAGENT PACK FOR IMMUNOASSAYS

This application is a continuation of U.S. patent application Ser. No. 07/709,726 filed Jun. 3, 1991 now abandoned.

REFERENCE TO RELATED APPLICATIONS

The following co-pending applications, filed on even date herewith, are specifically incorporated by reference:

"Retrofit Kit for Changing Single Immunoassay Instrument to Flexible Multiple Immunoassay Instrument" by Chadwick M. Dunn, Cass J. Grandone, Stephen L. Herchenbach, Robert J. Nelson, James T. Tyranski and Gary Lee Zuck, U.S. Ser. No. 07/709,730, now abandoned.

"Carousel for Assay Specimen Carrier" by Cass J. Grandone, James T. Tyranski, Stephen L. Herchenbach, Gary Lee Zuck, U.S. Ser. No. 07/709,729;

"Heat and Air Flow Control for Assay Carrier" by James T. Tyranski, Chadwick M. Dunn, Cass J. Grandone and Kris T. Ludington, U.S. Ser. No. 07/709,728;

"Reagent Bottle and Cap" by James T. Tyranski, now U.S. Pat. No. 5,145,646;

"Adaptive Scheduling System and Method for Operating a Biological Sample Analyzer with Variable Rinsing" by Cass J. Grandone, U.S. Ser. No. 07/710,195;

"Adaptive Scheduling System and Method for Operating a Biological Sample Analyzer with Variable Interval Periods, Kathleen L. Burns, Ilya Ratner, Jeanine T. Douglas, Erica Jean Kline, and Cass J. Grandone, U.S. Pat. No. 07/709,723;

"Adaptive Scheduling System and Method for a Biological Analyzer with Reproducible Operation Time Periods" by Cass J. Grandone, Mark Pierce, Ilya Ratner and Jeanine T. Douglas, U.S. Ser. No. 07/709,721.

BACKGROUND OF THE INVENTION

1. Field of the Invention

The subject invention is generally directed to containers for reagent packs and is specifically directed to a reagent pack for carrying reagents for immunoassays wherein the pack may be used for shipment of the assays and then installed in instrumentation during running of the immunoassay tests.

2. Description of the Prior Art

Biological sample analyzers, of the type considered herein, are automated instruments that may be used in hospitals, clinics, laboratories, or other locations, to run routine tests (assays) on samples of patient specimens such as blood, spinal fluid, urine, serum, plasma, and so on. An automated analyzer of the type discussed herein includes an analyzer unit that runs tests on a number of patient specimen samples that are loaded into the unit. An operator-user prepares the samples by placing portions of the patients' specimen samples into a number of like-sized sample containers. These samples may be diluted or otherwise treated, depending upon the type of analyzer used, the type of assay being performed, and other factors. The containers are then placed in the analyzer unit. The containers may first be placed in a rack or carousel that is then placed in the analyzing unit. The rack may accommodate a number of sample containers, e.g. 24. In addition, one or more appropriate chemical reagents, needed to perform the assays, are also placed in the analyzer unit. In order to mix reagents with the samples, the analyzer unit may also include a fluid moving system, such as a robotic probe mounted on a boom, which is adapted to draw up portions of the reagents and/or samples and expel them into appropriate locations, e.g. additional cells such as reaction cells provided in the sample containers, where a reaction can take place. The analyzer unit also may include a means for detecting a reaction in the reaction cells. This may include an optical detector to observe fluorescence reactions and make optical measurements to obtain a result for each sample. The analyzer unit may also typically include other mechanical systems to move the sample containers and the probe. The analyzer unit may also provide for cleaning the probe between certain tasks in order to avoid contamination between samples. For this purpose, the analyzer unit may also include a washing station and a waste dispensing container to hold the used rinse solution.

After the operator-user loads the specimen samples, enters appropriate instructions, and starts the unit, the analyzer runs unattended. When placed in operation, the analyzer unit, using the appropriate chemical reagent, runs the same test on each of the samples in the sample containers and will perform identical operations on each of the samples loaded in the rack. When it is finished, the analyzer prints out or otherwise reports on the results of its testing.

Biological analyzers utilize different chemistries for performing assays of specimen samples. One type of assays used in biological analyzers includes immunoassays and solid phase procedures. Analyzers for performing immunoassays in general and enzyme immunoassays in particular are known in the art.

A biological analyzer that utilizes immunoassay chemistry to perform assays of specimen samples loaded therein is the IMX ® analyzer introduced in 1988 by Abbott Laboratories, of North Chicago, Ill. (A description of the IMX ® analyzer is included in "The Abbott IMX ® Automated Benchtop Immunochemistry Analyzer System", by Fiore, M. et al, *Clinical Chemistry*, Vol. 34, No. 9, 1988, which is specifically incorporated herein by reference in its entirety). The IMX ® analyzer is a biological sample analyzer that has been developed for use in conjunction with solid phase immunoassay procedures to perform a variety of assays (such as sandwich and competitive assays). The IMX ® analyzer uses a technology referred to as microparticle capture enzyme immunoassay (MEIA) fluorescence polarization immunoassay (FPIA). The IMX ® analyzer includes a microprocessor used to control a robotic arm with two degrees of freedom and a rotating carousel to process the samples for assay. One assay can be done on each of 24 specimen samples in 30–40 minutes or more unattended after loading (i.e. with "walk away" automation). Assay results are output to a printer or a computer interface.

A biological sample analyzer, such as the IMX ® analyzer described above, can execute the steps required for performing assays of up to 24 specimen samples, including the steps of counting the samples, identifying which assay to run, warming the reagents and reaction cells to appropriate temperatures, pipetting the reagents and samples, diluting samples if required, timing critical assay steps such as incubations, washing unbound conjugate, quantifying the fluorescence signal and performing data reduction to yield a useful results.

The container used for holding each of the specimen samples for a biological sample analyzer, such as the IMX ® analyzer, may be a disposable assay cartridge having a plurality of wells, with at least one reaction well and a separation well. The separation well may contain a fibrous matrix positioned across its entrance and an absorbent material positioned below the fibrous matrix. Microparticles react with an analyte containing sample and one or more reagents to form an complex. This complex is immobilized on the matrix of the separation well. The excess sample and reagent are washed through the matrix and captured in the absorbent material below.

The results of the reactions may be read using known optical detection techniques. For example, using conventional solid phase procedures, an analyte can be labeled or tagged with an enzyme which, in the presence of its substrate, fluoresces and emits light at a known wave length. The rate at which the fluorescent product is produced is indicative of the concentration of the analyte in the biological sample. A conventional fluorometer is suitable for illuminating the fibrous matrix with a beam of light having the appropriate excitation wave length. The fluorometer also detects the intensity of the light at the emission wave length assays. Using this type of solid phase technology has been found to provide a high degree of sensitivity.

A biological sample analyzer, such as the IMX ® analyzer, provides for performing assays of patients' specimen samples and reading the results of such assays in a mass production type manner. This allows such assays to be quickly and conveniently available.

Even though such analyzers can provide significant advantages by performing assays quickly and conveniently, further advantages for the user could be obtained if the overall through put of the analyzer could be increased. One way to provide even more advantages and convenience for users of biological analyzers would be to provide the capability to perform more than one assay on the specimen samples in an unattended run. Although a biological analyzer like the IMX ® analyzer can perform different types of assays and can perform assays on a number of specimen samples unattended, the analyzer can run only one type of assay at a time. If a different type of assay is to be performed, the analyzer would have to be reloaded with different reagents. Also, because different types of assays may require different amounts of the sample specimen, different amounts of reagents, different processing steps, different incubation times, etc., the analyzer would also be reset at the beginning of the run to perform the new assay. In the case of the IMX ® analyzer, a different memory module may have to be inserted containing the instructions for the analyzer unit for performing the different assay. Thus, even if only a few of several different types of assays needs to be run, the operator-user has to load and run the analyzer for the first type of assay for only a few samples and then reload the analyzer to run the second type of assay on another batch of samples using perhaps different reagents. It is recognized that for many users of the IMX ® analyzer, or other biological sample analyzers, it would be convenient and advantageous to be able to perform more than one type of assay during an unattended run.

The disposable assay cartridges are particularly well suited for use in automated assay preparation and reading equipment. Due to the low amount of radiant energy produced by assays using the fibrous matrix technology, it is imperative in such automated equipment that the assay containing reaction well of each and every cartridge be positioned with a high degree of accuracy in each of three dimensions with respect to the optical reading apparatus in order to ensure that the readings have a repeatable high degree of accuracy.

The cartridges must not only be precisely positioned, they must be effortlessly and transparently positioned by even an unskilled operator with the same high degree of accuracy, in order to reduce the time and cost of each assay. That is, when the assays can be performed and read in a mass production-type manner, the unit cost for such assays decreases. In addition, the assay results can be made available more quickly.

A carousel for carrying a plurality of reaction cells for use in connection with the Abbott IMX ® System is disclosed in U.S. Pat. No. 4,956,148 entitled: "Locking Rack and Disposable Sample Cartridge" issued to C. J. Grandone on Sep. 11, 1990, and assigned to Abbott Laboratories, the assignee of the present invention.

While instrumentation such as the Abbott IMX ® System and the disposable reaction cell used in combination therewith have greatly advanced the art, each immunoassay test performed by the instrument takes approximately 30–40 minutes or more to run.

In many installations and applications, far fewer than 24 reaction cells are used at any one time. Therefore, the total capacity of the instrumentation is not used during a single immunoassay operation. However, the run time for those assays does not appreciably decrease. It has been found that clinical laboratories desire to run a plurality of different immunoassay tests simultaneously in small batch lots. Currently, the only way of doing such multiple assay runs is to run sequentially multiple carrousels, usually half empty, through the instrument.

SUMMARY OF THE INVENTION

The subject invention is directed to an immuno chemistry analyzer system that offers the capability of testing for up to three or four analytes in a single batch during a single run using currently available laboratory instrumentation. The subject invention will increase laboratory throughput and labor efficiency and will decrease technician attendance time. The system enables users to group three small batches of assays together rather than run three separate analyses. This allows results to be obtained approximately 25–50% faster when compared to the time required for running three individual batch assays on the single assay instrumentation.

The preferred embodiment of the invention includes a new reaction cell carrier with an integral reagent pack. Typically, the carrier comprises a carousel with multiple reaction cell capacity, such as by way of example, a batch capacity of up to 24 cells. A plurality of separate reagent packs may be incorporated in the carousel, and will utilize the same reagent components as the current individual batch assay reagent packs. Performance of the multiple test system is equivalent to the single batch counterpart. The same reagents, calibrators and controls are used for both systems. The precision, sensitivity and control ranges are comparable to the same assay currently run in the currently available prior art systems. By using the multiple test, multiple cell upgrade, the increased overall throughput and equivalent performance is a significant enhancement over available clinical laboratory instrumentation systems.

In its preferred form, the multiple test system comprises a reaction cell carrier such as a carousel having a plurality of reaction cell positions disposed about the outer perimeter thereof. In the center of the carousel are a plurality of reagent pack positions. In the preferred embodiment, three reagent packs are provided and are disposed 120° apart. Each reagent pack supports three reagent bottles for performing an immunoassay test in accordance with known practices. A common substrate reagent is supplied independently of the carousel.

In the preferred embodiment of the invention, each reagent pack can carry sufficient reagent for a yield of up to 100 tests. The carousel is adapted to carry reaction cells and typically carries up to twenty-four cells, each of which may carry any one of a plurality of specimens for performing any of a plurality of assay tests corresponding to the reagent packs loaded in the carousel, wherein the reaction cells may be loaded into the carousel in a preselected manner and the system is capable of "remembering" where each reaction cell is located once the location is stored in the system memory.

The reaction cells, carousel, reagent packs, and reagent bottles have been modified to accommodate selective multi-batch testing without requiring any other hardware changes to existing laboratory instrumentation currently in place in the field. This permits ready enhancement of currently available systems at a minimum of cost and retraining effort. In fact, current single test instruments may be converted to multiple test selective systems in a manner of minutes by installing a software program module, a bar code scanner and a new carousel in currently existing equipment.

The subject invention is particularly directed to a reagent pack which is specifically adapted to be removably installed in a carousel, wherein the carousel accurately positions the regents in the instrumentation for the running of a predetermined immunoassay. The reagent pack is adapted to receive and carry a plurality of reagent containers as determined by the specific immunoassay to be run. Each reagent pack includes a specific bar code label which permits machine reading of the critical data into the microprocessor of the immunoassay test instrumentation. The reagent pack is specifically designed to hold the individual reagent containers in a manner permitting maximum extraction of the fluids therefrom, increasing the efficiency of the operation.

It is, therefore, an object and feature of the subject invention to provide for a clinical laboratory immunoassay analyzer capable of running a plurality of analytes in a multiple specimen batch during a single run.

It is a further object and feature of the subject invention to provide for a multiple immunoassay test system capable of running a plurality of immunoassay tests on multiple samples utilizing currently available and installed clinical laboratory instrumentation.

It is a further object and feature of the subject invention to provide for a multiple batch, multiple pack carrier with controlled and predictable heating characteristics for minimizing the evaporation of components of the test and samples both during storage and testing.

It is yet another object and feature of the invention to provide a reagent pack for carrying a plurality of reagents in individual containers, wherein the reagent pack is suitable for both shipment of the reagents and for installation and use in currently available instrumentation.

Other objects and features of the invention will be readily apparent from accompanying drawings and description of the preferred embodiments.

BRIEF DESCRIPTION OF THE DRAWINGS

FIG. 10 is an exploded perspective view of a reagent and bottle pack adapted for use in combination with the carousel of FIG. 2.

FIG. 11 is a front perspective view of the reagent pack shown in FIG. 9.

FIG. 12 is a top view of the reagent pack.

FIG. 13 is a side section view of the reagent pack, taken generally along the lines 13—13 of FIG. 10.

FIG. 14 is an enlarged fragmentary view looking in the same direction as FIG. 13.

FIG. 15 is a view similar to FIG. 13, showing a bottle installed in the reagent pack.

FIG. 16 is a section view taken generally along the line 16—16 of FIG. 13.

FIG. 17 is a side view of a bottle and cap adapted for use in combination with the reagent pack of FIGS. 10-16.

FIG. 18 is an enlarged top view showing the detail of the cap for use in combination with the bottle of FIG. 17.

FIG. 19 is a sectional view taken generally along the line 19—19 of FIG. 18.

DESCRIPTION OF THE PREFERRED EMBODIMENT

Figure 1:
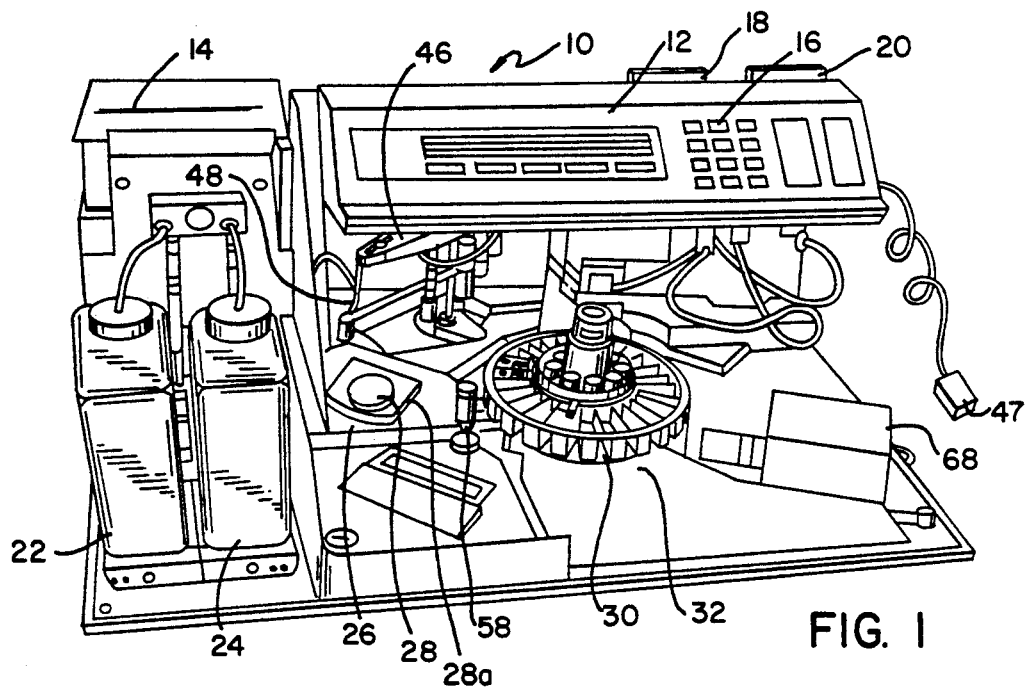
FIG. 1 is a perspective view of a clinical laboratory instrument for automated immunoassay testing, utilizing the multiple cell and reagent pack system of the subject invention.

A clinical laboratory automatic immunoassay testing instrument of the type for use in combination with the batch, multiple reaction cell and multiple reagent carrier of the subject invention is shown in FIG. 1, as designated by the reference numeral 10. In the preferred embodiment of the invention, the instrument 10 comprises an Abbott IMX ® System manufactured by Abbott Laboratories, North Chicago, Ill., 60064. The instrument comprises a control panel 12 containing a switchable power supply, a microprocessor, a data printer 14, an operator actuated input panel 16 and a plurality of ports 18 and 20 for user installable and user replaceable software modules. In the current system, dual diluent buffer bottles are provided at 22 and 24 and a heater block 26 is provided for housing a reagent pack which includes substrate reagent bottle 28 in a substrate carrier 28a. In the preferred embodiment, the multiple cell, multiple reagent pack carousel carrier 30 is adapted to be inserted in the instrument 10 above a heating plate 32 in the same manner as the current carousel is inserted in the existing IMX ® instrument.

Figure 2:
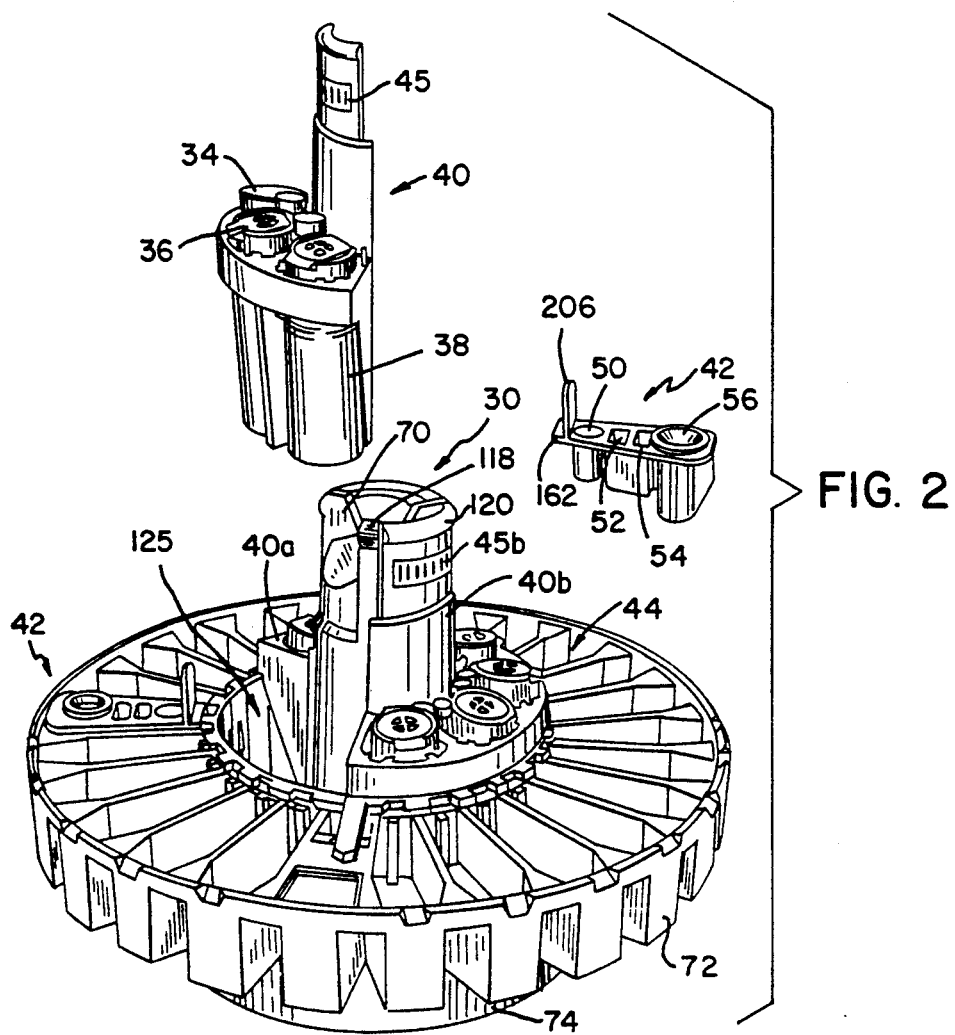
FIG. 2 is an exploded perspective view of a multiple station reaction cell and reagent pack carousel carrier for use with the instrument of FIG. 1.

As shown in FIG. 2, in accordance with the subject invention the components for a reagent test are supplied in a plurality of bottles 34, 36 and 38 disposed in a reagent pack 40 carried in the carousel 30. A plurality of reaction cells 42 are disposed in the cell receptacles 44 in the compartmentalized perimeter of the carousel 30, positioned radially outwardly from the reagent pack 40. In its preferred form, the carousel 30 is adapted to house three reagent packs 40, 40a and 40b (FIG. 2), spaced 120° about the axis of rotation of the carousel. Each reagent pack 40, 40a, and 40b includes a unique bar code label 45, 45a (not visible in FIG. 2), and 45b, respectively. A hand-held bar code reader 47 is used to read the labels for reading the reagent data into the instrument microprocessor.

The instrument 10 includes a robotic arm 46 having a fluid transfer system including a pipet type probe 48. The robotic arm 46 is adapted for moving the pipet 48 in a radial path and for accurately adjusting the vertical height of the pipet, permitting communication of the probe with the substrate reservoir 28, each of the bottles 34, 36 and 38 housing a reagent component and each of the compartments or wells 50, 52, 54 and 56 of a reaction cell 42, in order to distribute the various components and specimen samples between various positions in order to complete the desired immunoassay test. The robotic arm 46 is also adapted to move the probe 48 into contact with the wash and waste drain 58 provided in the instrument 10.

It is an important feature of the subject invention that the carousel configuration of FIG. 2 be adapted to be received and utilized by the currently available IMX ® laboratory instrument, without modification of the hardware contained therein. Thus, the orientation of the reagent packs 40, 40a and 40b carried in the carousel 30 are specifically designed to be accessible by the robotic arm 46 and pipet probe 48 as currently available in installed systems. Also, because of the movement of the reagent components from the heat block 26 to the center of the carousel 30, specific design features are provided in the carousel design to provide for proper temperature control of the reagent packs by the heating plate 32. Typically the heating block 26 is used to heat the substrate 28. The reagents in packs 40, 40a, and 40b may or may not be heated, depending on application. The heating block 26 and the heating plate 32 are heated to a predetermined temperature level for maintaining the reagent substrate, reagent pack components and specimen cells at an even controlled temperature through the testing operation.

Figure 3:
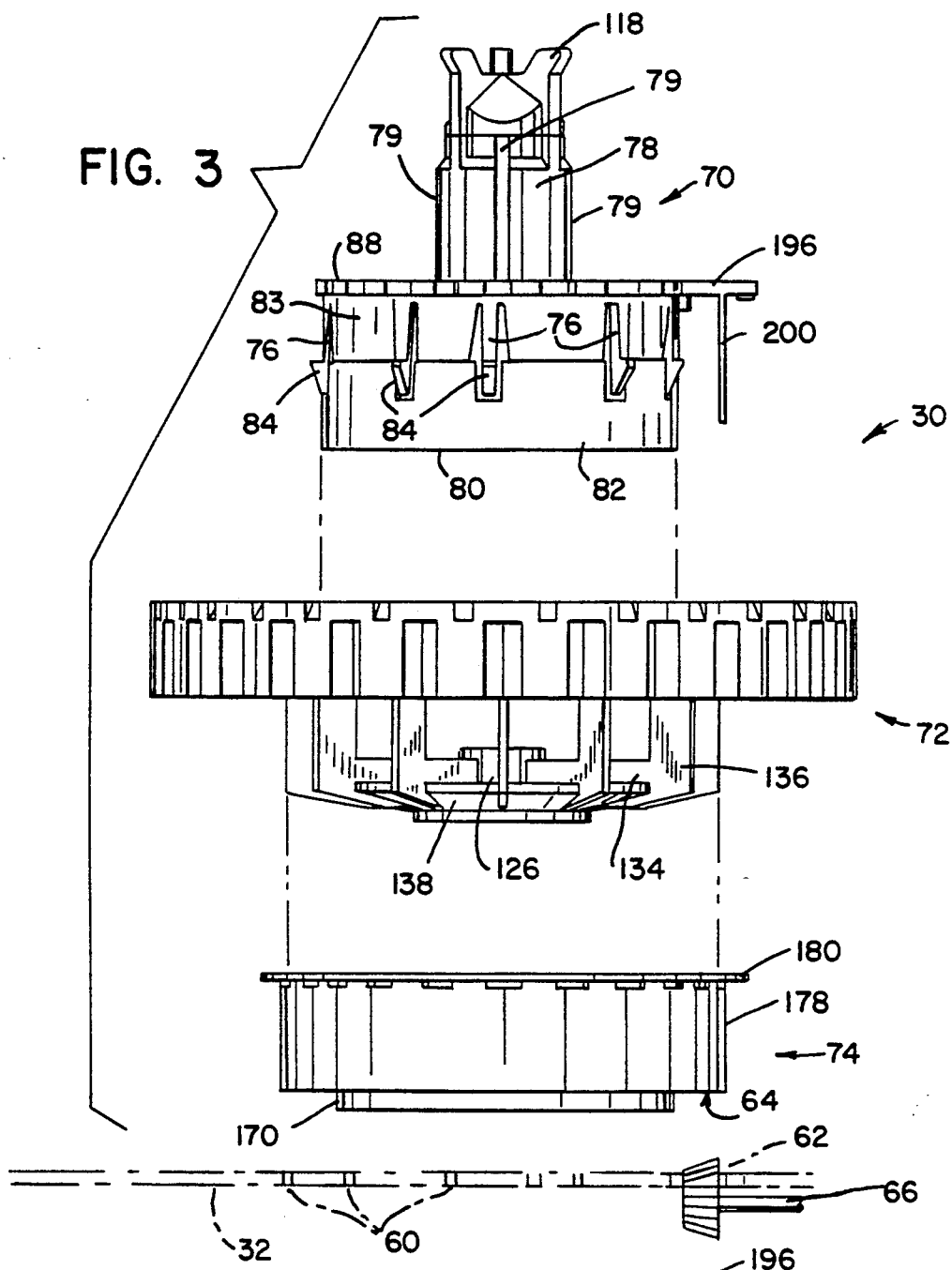
FIG. 3 is an exploded elevation view of the carousel of FIG. 2, with a portion of the instrument shown in phantom.

As shown in phantom in FIG. 3, the heating plate 32 comprises a flat plate with a plurality of evenly dispersed apertures 60 for providing a flow of warm air up through the carousel. Also as shown in FIG. 3, a drive gear 62 is provided and passes through a suitable opening provided in the plate 32 for engaging a drive ring 64 (see FIG. 7) provided on the underside of the carousel. In a typical installation, the drive gear 62 is mounted on a drive shaft 66 which is in communication with a drive motor (not shown) controlled by the control system of the instrument 10. As the robotic arm is moved from position-to-position relative to the various wells in the reaction cells, the reagent pack bottles and the substrate bottle, the drive gear 62 is driven by the motor to index the carousel in order to provide proper alignment of the pipet probe 48 with the various positions of the carousel 30.

A more detailed description of the interrelationship of the drive gear 62, the pipet probe 48, robotic arm 46 and control system may be found in the published article entitled: *The Abbott IMX ® Automated Benchtop Immuno Chemistry Analyzer System*, Clinical Chemistry, Vol. 34, No. 9, 1988, pps. 1726–1732.

The carousel, reagent pack and bottle system and the software program module upgrades of the subject invention permit modification of single immunoassay test instrument to a multiple test, multiple reagent pack system by removing the currently installed carousel and replacing it with the carousel of the subject invention. This is particularly advantageous since the carousel currently is readily removable in order to permit easy installation and removal of the disposable reaction cells. Therefore, no hardware alterations are required of the instrument 10, per se, in order to upgrade the capability of currently installed systems to provide for a clinical instrument which can perform a variety of different immunoassay tests simultaneously on a plurality of reaction cells carried by a single carousel 30. All other changes to the system are provided by installing user installable software modules at the ports 18 and 20 presently available in the instruments of the prior art and by providing the portable, hand-held bar code reader 47 for reading the reagent pack labels 45.

Turning now to the preferred embodiment of the carousel assembly, the carousel 30 is shown in perspective in FIG. 2. As there shown, the carousel comprises a plurality of reaction cell compartments 44, each adapted for housing a single reaction cell 42, in the well known manner. The reaction cells are more particularly described in U.S. Pat. No. 4,956,148 entitled "Locking Rack and Disposable Sample Cartridge" issued to C. J. Grandone on Sep. 11, 1990 and assigned to the assignee of the subject invention, incorporated by reference herein. By way of general description, each reaction cell 42 comprises a unitary receptacle having a plurality of wells 50, 52, 54 and 56. The well 56 is an assay reaction well and includes a funnel top, a fibrous matrix and an underlying absorptive material, as described in the aforementioned U.S. Pat. No. 4,956,148. The reaction well 56 is provided to contain an assay for reading under an optical reading apparatus such as the photometer 68 of the instrument 10 (FIG. 1).

As best shown in FIG. 3, in its preferred form the carousel 30 comprises three components each manufactured of a molded thermoplastic material: the bucket 70, the reaction cell carousel 72 and the drive ring/heat deflector 74. The particular configuration of the preferred embodiment permits each of the components 70, 72 and 74 to be constructed of a material best suited for the specific function of the component. For example, the bucket 70 comprises an assembly constructed of molded ABS plastic components which are rigid, yet resilient, permitting the incorporation of a plurality of flexible, live spring tabs 84 for permitting snap-in assembly of the bucket in the carousel 72. The carousel 72 is made of a unitary molded ABS plastic material. The unitary drive ring/heat deflector 74 is made of a TFE filled ABS material which readily permits a molded construction having a gear ring 64 (FIG. 7) with drive track slots 65 which can be maintained within ±0.001 accuracy for providing an accurate indexing track for the carousel assembly. The TFE filled ABS material has better wear characteristics than the ABS plastic, increasing the durability of the ring.

Figure 4:
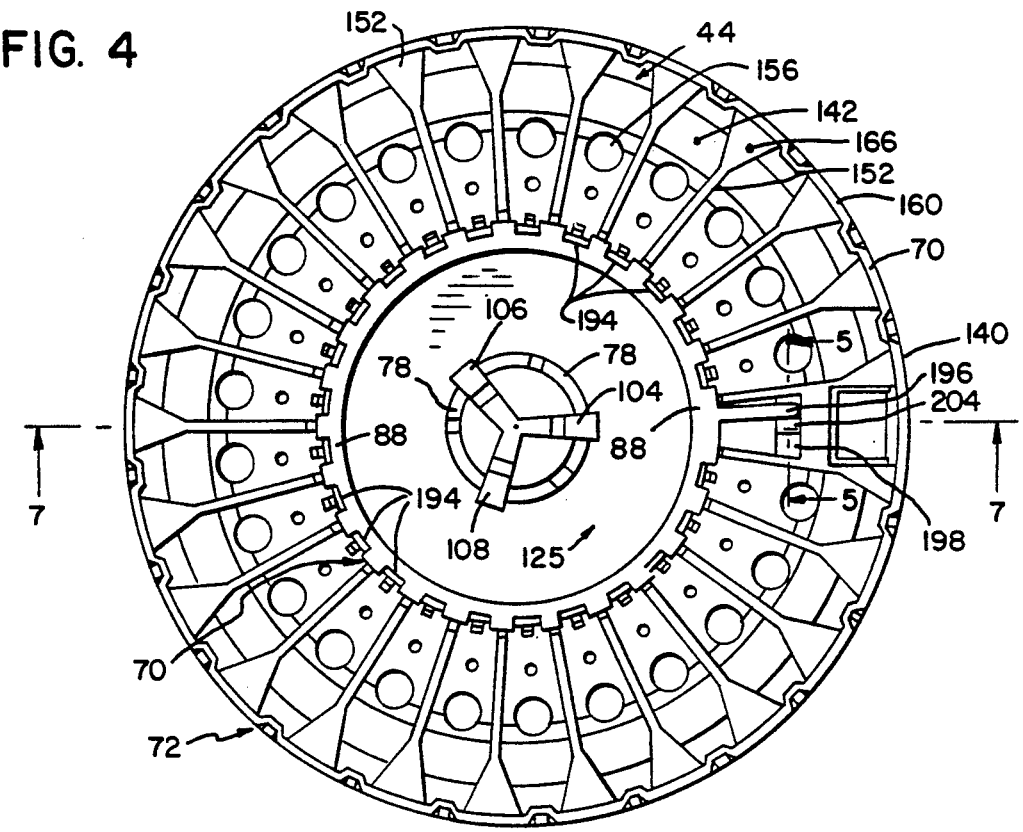
FIG. 4 is a top view of the assembled carousel of FIGS. 2 and 3.
Figure 7:
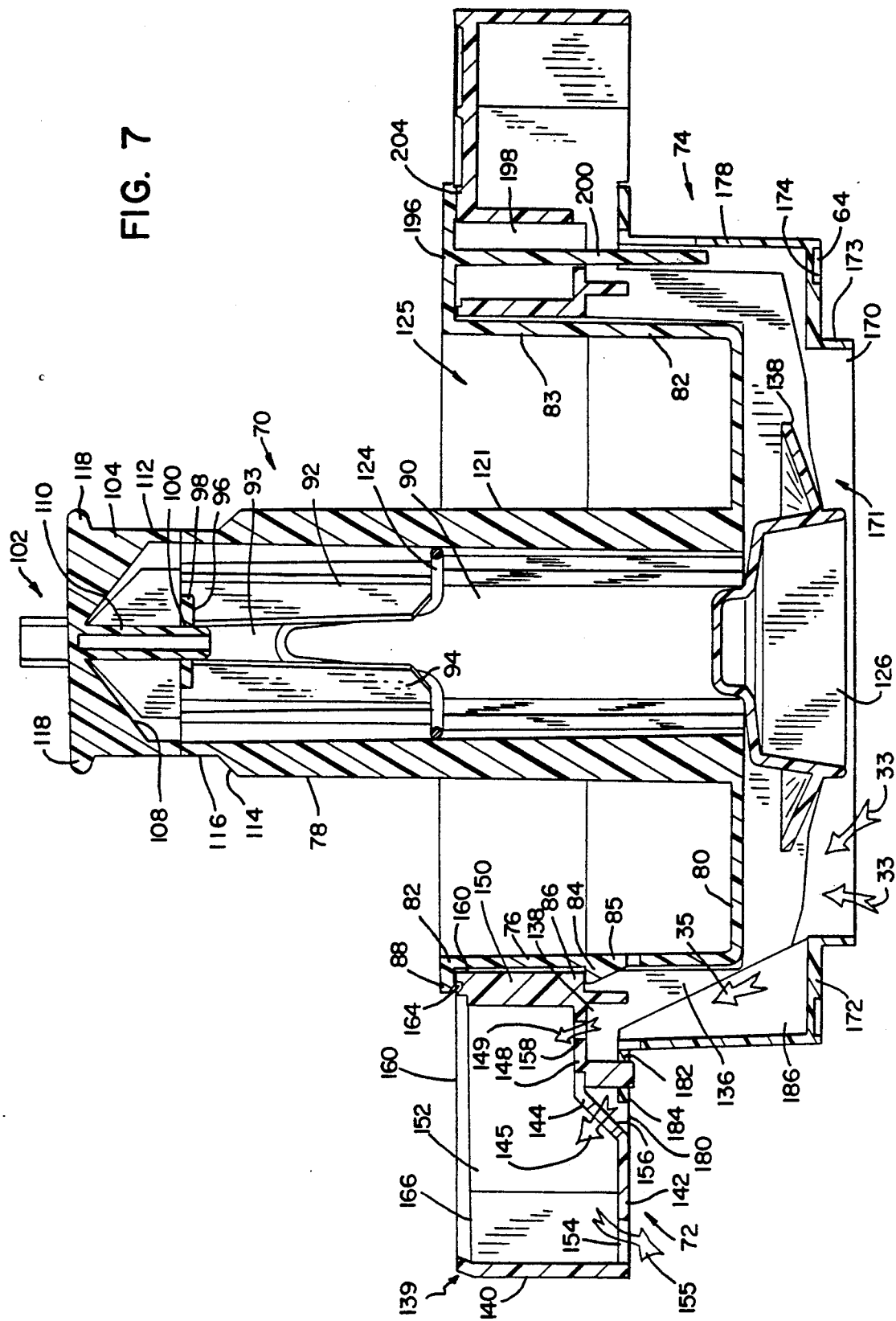
FIG. 7 is a section view of the assembled carousel, taken generally along the line 7—7 of FIG. 4.

The preferred embodiment of the bucket 70 for the reagent packs 70 is best shown in FIGS. 3, 4 and 7. As there shown, the bucket comprises a center spindle 78 with a hollow core 90, a substantially horizontal base 80 (FIG. 7) radiating outwardly from the spindle 78 and an external cylindrical side wall 82. A substantially cylindrical ring 83 is mounted on side wall 82 and includes a plurality of integral live springs 76. Each of the springs 76 terminates in a projecting tab 84 which is adapted to engage a projecting abutment corner 86 on the carousel 72 (see FIG. 7). A radially outwardly projecting lip or rim 88 is provided along the top edge of the ring 83 and is adapted to engage the upper edge 160 of the side wall of the carousel 72 (also see FIG. 7). This construction permits the bucket 70 to be snap fit into the carousel 72 by sliding the inclined surfaces 85 of tabs 84 into the carousel, providing a semi-permanent assembly, wherein removal of simultaneously retracting all of the spring tabs 84 from engagement with the abutment corner 86 of the carousel to facilitate axial removal of the bucket from the carousel assembly.

As is best shown in FIG. 7, the spindle 78 includes a hollow center core 90. In the preferred embodiment, the spindle 78 includes a tapered step 114 and a reduced cylindrical portion 116. Projecting radially inwardly from the spindle wall 78 are a plurality of substantially vertical ribs 92, 93 and 94 (see FIG. 4). Each of the ribs includes a recess 96 (FIG. 7) for defining a flat, substantially horizontal mounting surface for receiving the annular mounting ring 98. The annular mounting ring includes a central through opening 100. A separate spindle cap 102 comprises a plurality of ribs 104, 106 and 108 (FIG. 3), and a central vertical post 110 which is adapted to be inserted in the aperture 100 of the annular ring 98. Each of the ribs 104, 106 and 108 each comprises an outer, substantially vertical upstanding wall 112 (FIGS. 4 and 7) which is in substantial alignment with the reduced portion 116 of the outside wall of the spindle 78. The upper end of each of the ribs 104, 106 and 108 includes an outwardly radially projecting tab 118.

Figure 9:
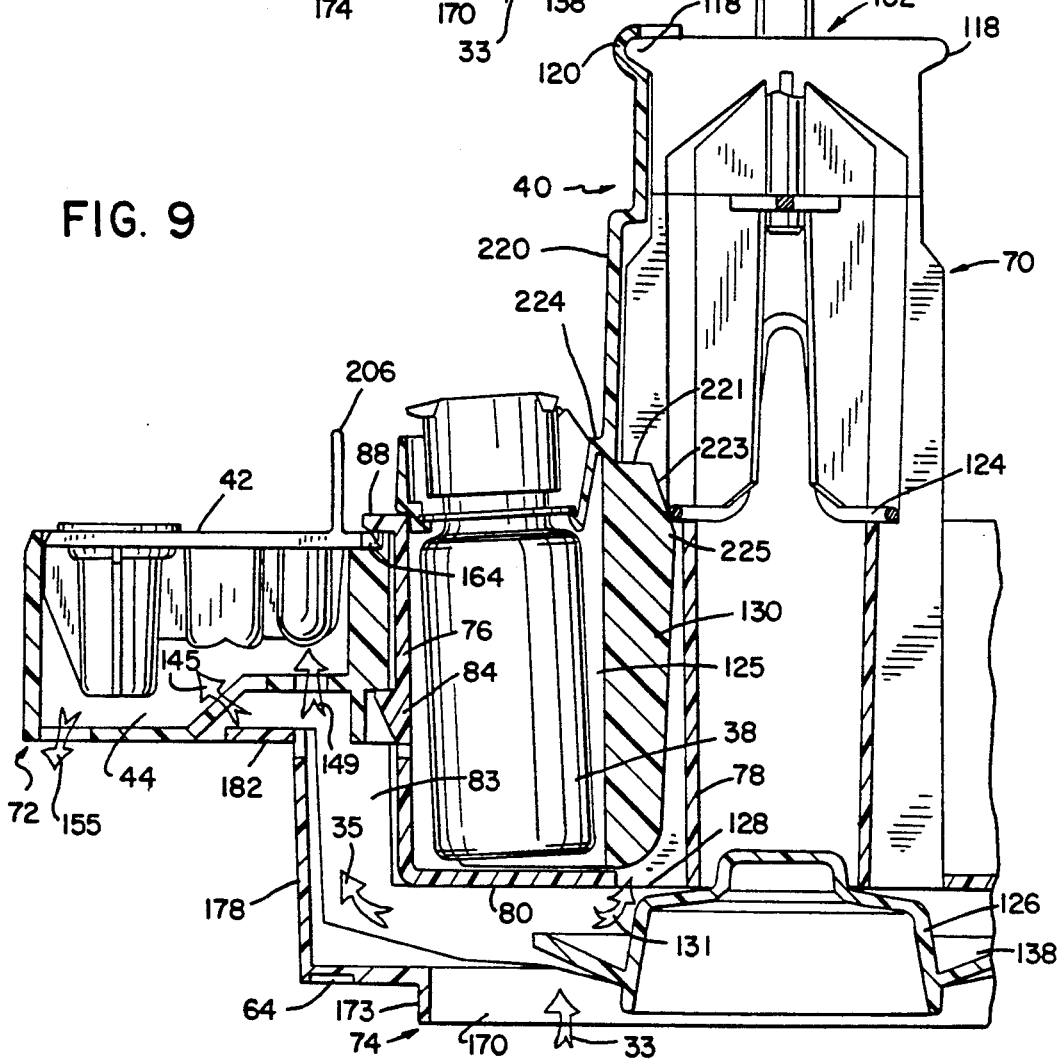
FIG. 9 is a partial view looking in the same direction as FIGS. 7 and 8, showing yet another alternative embodiment of the carousel and showing the reaction cell and reagent pack installed in the carousel.

The assembled bucket 70 is adapted to be permanently mounted in the carousel carrier 72 for housing and carrying the removable reagent packs. As is best shown in FIG. 9, the tab 118 is adapted to be aligned with the annular lip 120 on the reagent pack 40 to give a visual indication of proper placement of the pack in the bucket. As shown in FIG. 7, the lower outside wall 121 of the spindle 78 and the outside perimeter side wall 82 of the bucket define an annular well 125 having a bottom defined by the base 80 for housing and enclosing the bottles 34, 36, 38 carried by the reagent pack 40 (see FIG. 9). In the preferred embodiment, the bucket 70 is designed to carry three reagent packs 40, 40a, 40b (FIG. 2), each of which occupy an included angle of 120° of the annular well of the bucket.

As is best shown in FIG. 3, the spindle 78 includes a plurality of vertical, angular spaced through slots or channels 79. A formed bent spring 124 (FIG. 9) is mounted in the spindle at the base of ribs 92, 93 and 94 and has outer ends in communication with the channels 79. As is best shown in FIGS. 9, 13, 14, and 15, the reagent pack 40 includes an upstanding wall 220 having an inwardly radially projecting ridge 221 and an inclined surface 223 terminating at the reduced internal diameter section 225. As shown in FIG. 16, the pack 40 includes a vertical rib 231 centrally located on the rear of wall 220. When the pack 40 is installed in the bucket 70, the rib 231 is inserted in one of the slots 79 for properly angularly positioning the pack. The ridge 221 extends into the space beneath one of the ribs 92, 93, or 94 and the inclined surface 223 engages spring 124 (see FIG. 9). The spring provides a downward force against the surface 223 to lock the pack in place. Proper alignment is assured by the visual alignment indicator provide by tabs 118 on the top of the bucket and lip 120 on the top of the pack.

Figure 8:
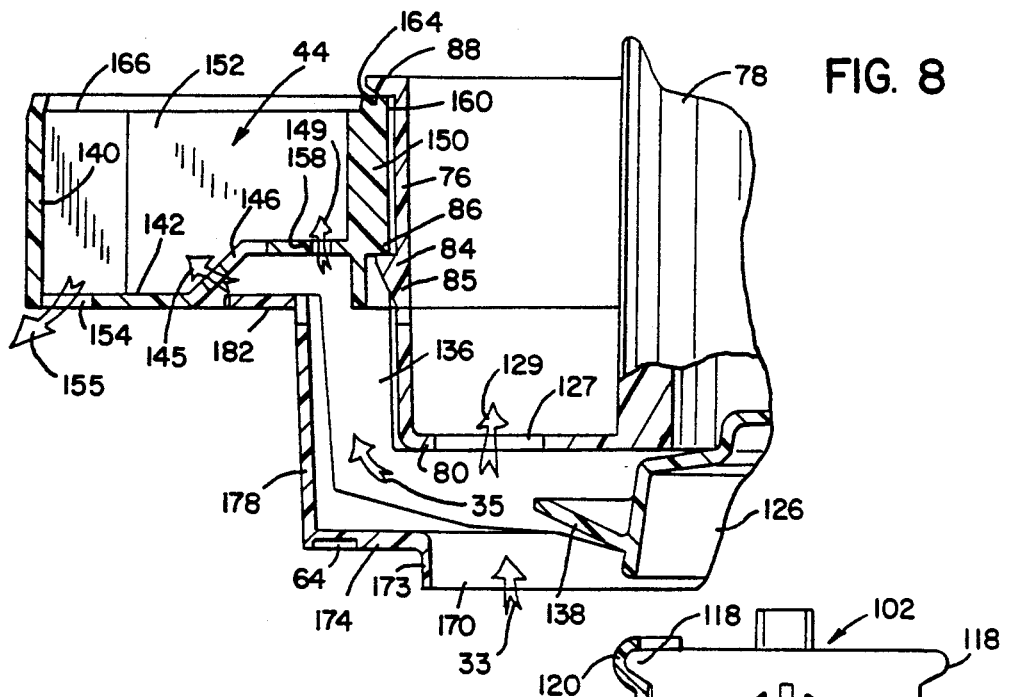
FIG. 8 is a partial view looking the same direction as FIG. 7 and showing an alternative embodiment for the carousel.

As is best shown in FIGS. 7, 8 and 9, the configuration of the base 80 of the bucket can be altered to provide for different heat flow characteristics depending on the temperature control requirements of the reagents in the bottles 34, 36 and 38 of the specific reagent packs to be used. As shown in FIG. 7, the base 80 can be a solid wall with a minimum opening between the hub 126 of the carousel and the open core 90 of the spindle 78 to minimize the flow of warm air into the region adjacent the bottle well 123. Where direct heating of the bottles is desired, the configuration of FIG. 8 may be utilized, which includes a plurality of openings 127 disposed about the annular base 80 for providing air flow directly into the bottle well and into direct contact with the bottles of the reagent pack, as indicated by arrow 129. An intermediate heating configuration is shown in FIG. 9, wherein openings 128 are provided between the spindle 78 and the base 80, permitting heated air to flow between the inner side wall 130 of the reagent pack and the spindle 78, but not into direct contact with the bottles 34, 36 and 38, as indicated by arrow 131. Each of these configurations permits different temperature control parameters to be met for controlling the temperature of the reagent packs when installed in the instrument 10.

The carousel carrier 72 is best shown in FIGS. 3, 4, 7, and 9. As there shown, the carousel comprises a bell shaped center hub 126 which defines the mounting hub for installing the carousel in the instrument 10. The hub has a plurality of spokes 134 radiating horizontally outwardly therefrom and a plurality of upstanding ribs 136 projecting vertically upward from each of the radiating spokes 134 (see FIG. 3). In the preferred embodiment, the hub 126 has a closed top to prevent the flow of heated air into the hollow core 90 of the bucket spindle 78. An annular deflector ring 138 is disposed outboard of the hub 126 and is angled slightly upwardly, as shown, to deflect and direct heated air from the plate 32 (shown in phantom in FIG. 3) upwardly and outwardly toward the perimeter of the carousel as indicated by arrows 33 and 35 to facilitate heating of the reaction cells 42 carried therein.

As best shown in FIG. 7, each of the upwardly extending ribs 136 terminates in an outwardly projecting support brace 138. The braces 138 carry an annular compartmentalized ring 139 which is disposed about the perimeter of the carousel 72 for defining the plurality of a cell compartments or receptacles 44. In the preferred embodiment, each cell receptacle 44 is defined by the outside side wall 140 of the ring, a base or bottom 142, a stepped wall 144, a raised bottom wall 148 and an inside annular side wall 150. Each of the receptacles are separated by an elongate radially extending side wall 152. As shown in FIG. 9, each receptacle 44 is adapted to accommodate a single reaction cell 42 in the manner well known and as described in the aforementioned U.S. Pat. No. 9,956,148. In the preferred embodiment, the bottom walls 142, 146 and 148 of each cell receptacle may be provided with through apertures 154, 156 and 158, respectively, to facilitate air flow for temperature control.

The inner side wall 150 of the cell receptacle ring includes the lower abutment corner 86 for receiving and engaging the projecting spring tabs 84 of the bucket 70. The upper edge 160 of the wall 150 is disposed to engage the annular lip 88 of the bucket, whereby the bucket is held in rigid assembly with the carousel when tabs 84 and lip 88 are engaged by corner 86 and edge 160, respectively, of the reaction cell receptacle.

As is best shown in FIGS. 2 and 9, each reaction cell 42 includes a peripheral rim 162 which is adapted to be seated on and be engaged by the locator surface provided by the recess 164 (FIG. 9) in the end wall of the cell receptacle and the upper edge 166 of each of the plurality of radially extending walls 152. The ribbed construction of the carousel provides ample open air space between the structural members of the carousel and the drive ring/heat deflector 74 to provide air flow from the plenum into the carousel 72 and cell receptacles 42 to provide for consistent and accurate temperature control of the various components of the assembly. As indicated by arrows 145 and 159, the heated air flows into each compartment and generally upwardly and outwardly as it passes under the cell 42 (FIG. 9). The air is exited outside the plenum wall 178 through holes 154 as indicated by arrow 155.

Figure 6:
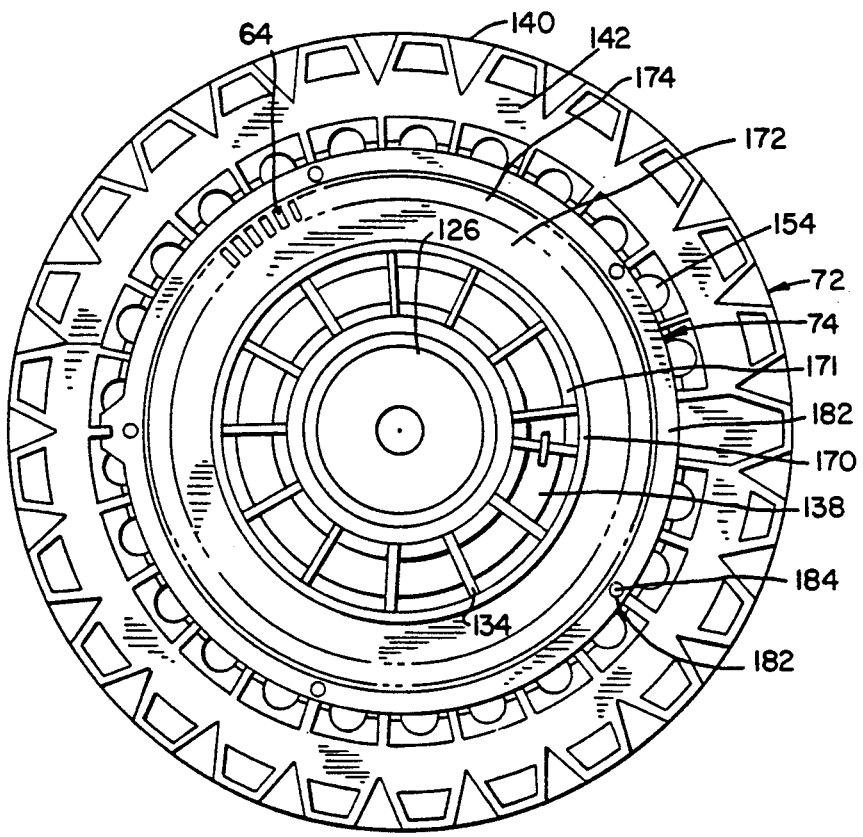
FIG. 6 is a bottom view of the assembled carousel of FIGS. 2 and 3.

The drive ring/deflector 74 is best shown in FIGS. 3, 6 and 7. As best shown in FIG. 3, the drive ring comprises an open annular ring 170 which has a central opening 171 (FIG. 7) large enough to accommodate the lower portion of the hub 126 of the carousel. The hub is then free to be seated on a locator spindle (not shown) in instrument 10 in the manner well known. The ring 170 has an upstanding outer side wall 173 (FIG. 7) from which radiates a substantially flat, horizontal drive ring plate 172. As is best shown in FIGS. 6 and 7, the drive ring plate 172 includes a circular drive track or rack 174 which is comprised of the plurality of accurately dimensioned, equally spaced indentations 64 disposed along the annular perimeter of the ring. In the preferred embodiment, the circular rack comprises a plurality of slots or indentations 64 each of which are adapted to engage the drive gear 62 in order to position and index the carousel as the various tests are performed. An upstanding substantially solid annular side wall 178 is disposed outwardly of the drive ring plate 172 and provides a closed plenum for directing air flow into the interior of the carousel 72, as previously described.

The upper end of the outer side wall 178 terminates in a substantially horizontal outwardly projecting mounting rim 180 (FIG. 3) which is provided with a plurality of mounting holes 182. The carousel 70 is provided with a plurality of spaced locator and mounting posts 184 (see FIG. 7) which are adapted to be received by the mounting holes 182 in the ring 180 for mounting and accurately aligning the drive ring/air deflector on the carousel. The carousel may be glued, sonic welded or secured by other suitable means to the drive ring to maintain the ring/deflector 74 and carousel 72 in permanent assembly. A plurality of reinforcing ribs 186 may be provided in and spaced radially about the perimeter of the ring/deflector 74 to provide rigidity in the molded construction.

Figure 5:
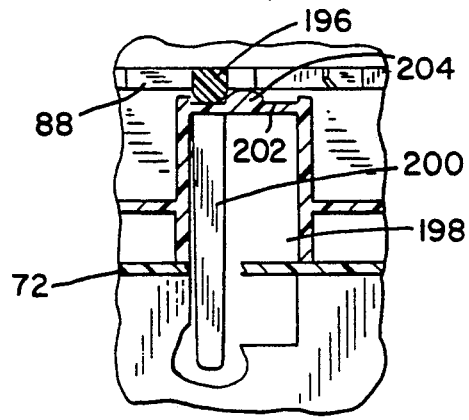
FIG. 5 is a partial section view taken generally along the line 5—5 of FIG. 4.

In the preferred embodiment of the invention, the outer lip 88 of the bucket 70 (FIGS. 3, 7 and 9) defines a locking ring which is adapted to extend beyond the projecting rim 162 of each reaction cell for locking each of the cells in the reaction cell compartments 44 of the carousel. As best shown in FIG. 4, a plurality of spaced notches 194 are provided around the outside perimeter of the ring or lip 88 and are adapted to be centrally located within each of the reactor cell receptacles when shown as positioned in FIG. 4. An elongate arm 196 extends outwardly from the ring 88 into a chamber 198 provided in the carousel assembly. As is best shown in FIGS. 5 and 7, the arm 196 has a downwardly extending finger 200. The locking chamber 198 of the carousel assembly includes a raised sliding surface 202 with a center bump 204. When the arm 196 is disposed to the left position as shown in FIG. 5, the notches 194 are moved off center from the cell compartment 44, causing the projecting outer perimeter of the ring 88 to be disposed in the center of the receptacle cells. The ring 88 then engages and locks the perimeter rim 162 of the reaction cells (FIG. 2) in each of the compartments 44 in the compartmentalized ring of the carousel. When the arm 196 is moved over the bump 204 and into the rightmost position (as shown in FIG. 4) the notches 194 are centered relative to the compartments 44, permitting removal of the reaction cells 42 by grasping each cell by the upstanding tab 206 (FIG. 9) and tilting it outward from the carousel. Thus, the bucket assembly 70 provides the locking ring for selectively locking and positioning the reaction cells in the carousel. In the preferred method of use, after completion of a run, the locking ring is unlocked and the carousel is inverted, allowing the cells to fall free from the carousel.

The reagent pack, bottle and cap assembly of the preferred embodiment are best shown in FIGS. 9-21. In the preferred embodiment, the reagent pack 40 is designed to accommodate three reagent bottles 34, 36 and 38. Each reagent pack 40 occupies an included angle of 120° in the circumferential well of the reagent pack carrier bucket 70. Once the lab assay testing unit 10 is converted to accommodate multiple immunoassay tests utilizing the carousel configuration 30, the various reagent packs 40, 40a and 40b are designed for installation and removal in the carousel to accommodate a plurality of immunoassay tests and to permit ready replacement of the exhaustible reagent components in the bottles 34, 36 and 38.

In its preferred form and as best seen in FIGS. 13-16, the reagent pack 40 comprises a integrally molded unitary carrier having a free-standing, an upstanding, annular vertical wall or framework 220 which is adapted to be placed with its inner side wall 130 adjacent the spindle 78 of the carousel bucket 70 (FIG. 2). As is best shown in FIGS. 11 and 13, the upper end of the wall 220 terminates in an annular ring or lip 120 adapted to be aligned with the extending tab 118 of the bucket cap (FIG. 9) when the pack is installed in the bucket. The upstanding wall 220 also includes a ridge 221 extending radially inward from the wall and terminating in the sloped surface 223 which is adapted to receive and engage the spring 124 provided in spindle 78. Just above the ridge 221 and extending radially outwardly from the wall 220 is a bottle retainer surface 224. The bottle retainer includes an outer rim 226 along its lower outside edge which is adapted to receive and engage the top edge of the outer lip or ring 88 of the bucket 70 (FIG. 9). This permits the reagent pack 40 to be inserted and snap fitted into the bucket well, assuring a rigid assembly when the reagent pack is installed in the carousel. The reagent pack includes a plurality of vertically extending ribs 226, 228, 230 and 232 (FIGS. 10 and 11) which provide for structural rigidity to the assembly as well separation of the three reagent bottles 34, 36 and 38. The ribs also form legs permitting the pack to be free-standing.

In the preferred embodiment, the reagent pack is adapted to accommodate three bottles 34, 36, 38, each of which is of a general cylindrical shape and includes a closed bottom 232 (FIGS. 15 and 17). The neck of the bottle is slightly reduced as at 234 and has an annular rim 235 disposed between the reduced portion 234 and the open mouth of the bottle. A plurality of seats 236, 236a, 236b and 238 are provided in the carrier 224 (FIGS. 11, 12 and 13), the seat 236 adjacent the mounting edge 226 being disposed at a point lower than the seat 238 adjacent the vertical internal wall 220 of the carrier. This assures that the bottle is disposed at an inclined angle relative to the vertical axis of the carousel, whereby the fluid in the bottle tends to accumulate in the valley created by the tilted angle, permitting maximum recovery of the fluid by a pipet probe. In the preferred embodiment the bottles are tilted at approximately 3°. As best shown in FIGS. 9, 12, 13 and 14, the carrier 224 also includes a plurality of retainers 240, 242 defined by offset, depending walls in the carrier. The central opening 243 (see FIGS. 12 and 14) of the carrier is large enough to accommodate the cylindrical barrel portion 245 of the bottle (the bottle is disposed as shown in phantom in FIG. 14) and the rim 235 is snap fit over and between the retainers 240, 242 and is seated on the seats 236, 236a, 236b and 238. This retains the bottle in a secure relationship relative to the reagent pack carrier 40.

Figure 20:
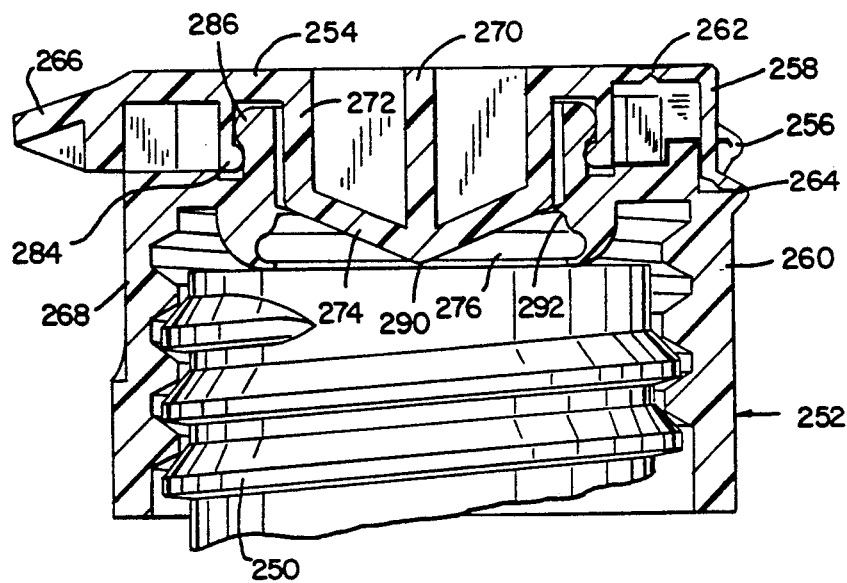
FIG. 20 is a section view of the cap taken generally along the line 20—20 of FIG. 18.
Figure 21:
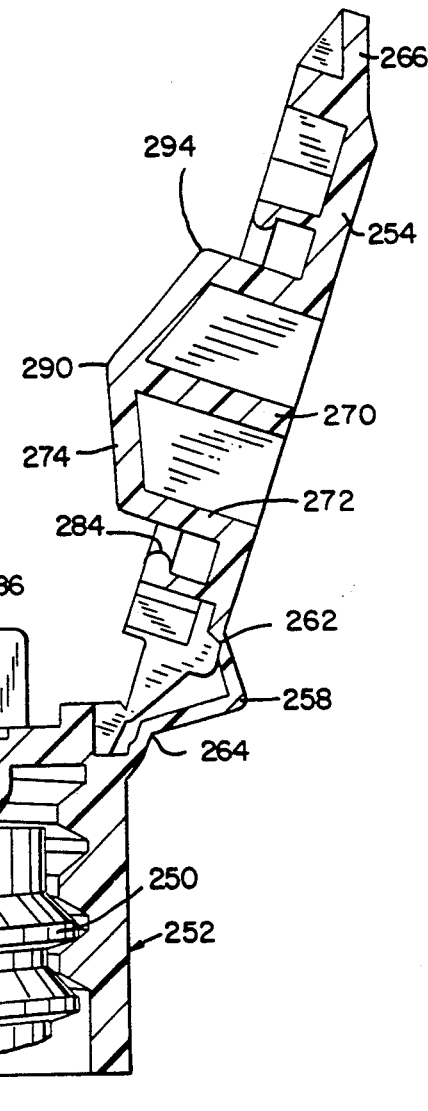
FIG. 21 is a view similar to FIG. 20, showing the cap in an open position.

The open neck of the bottle includes a male threaded portion 250 (FIGS. 19, 20 and 21) for accommodating the threaded cap 252. In the preferred embodiment, the cap 252 is a cylindrical threaded closure with a hinged flip top 254 (FIG. 18). It is contemplated that the cap be of a molded unitary construction with the hinged flip top being movable between the closed position of FIGS. 19 and 20 and the open position of FIG. 21, utilizing the integral live hinge 256 (FIGS. 18, 20, 21). As there shown, a pair of rectangular integral brackets 258 are provided between the closure top 254 and the cap body 260 to form a bi-stable spring which acts as an over-center biasing spring. The closure cap has a reduced V-section at 262 and at 264, whereby the bracket 258 serves as an over center spring for holding the cap in the open position. Thus, the combination of the live hinge 256 and the bracket 258 provide for a bottle cap 252 with a flip top 254 which is normally held in the closed position but will be maintained biased in the open position once the cap is opened far enough for the bi-stable brackets 258 to co-act against the action of the live hinge 256 and function as an over center spring, whereby the cap is held opened in the position of FIG. 21. The flip top 254 of the cap includes an elongate tab 266 diametrically opposite the live hinge 256. The outer side wall of the cap is recessed at 268 (FIGS. 17 and 21) to accommodate insertion of the thumb along the side of the cap to permit the user to flip the top 254 open by exerting thumb pressure against the tab 266. The outer side wall of the cap is vertically knurled, as shown at 269 (FIG. 17), to accommodate tightening of the cap on the bottle.

In the preferred embodiment, the top of the cap includes an integral molded cross pattern 270. This permits the user to center the instrument probe relative to the bottle by using the cross 270 as a locator after the reagent pack has been inserted in the carousel. The cross is placed on the cap such that the center of the cross will permit a vertically extending pipet probe to enter the cap at a region adjacent the lowest part of the valley created by the tilted bottle, to facilitate removal of the greatest amount of usable reagent fluids from the bottle during use.

In order to minimize evaporation of the reagent fluids in the bottle, the cap is provided with a double seal/wipe configuration as shown at 292 of FIGS. 19-21. The flip top closure portion of the cap includes a cylindrical core 272 which is highly polished to shed liquids. The highly polished core terminates in the also highly polished conical tip 274. The central aperture 276 of the cap is substantially cylindrical in shape and is adapted to be close fitting when received in the cylindrical core 272, reducing fluid entrapment space therebetween. This is accomplished by placing the live hinge 256 above and behind the center point of the cap, permitting a close fit while preserving the ability to incorporate a hinged, pivotal cap. As is best seen in FIGS. 19 and 21, an external annular upstanding wall 278 is provided outboard of the flip top 254 and extends from approximately the tab 266 to the brackets 256. A like outer wall 280 is provided on the opposite side of the cap flip top. Disposed between the outer walls 278, 280 is the inner upstanding cylindrical neck opening for accommodating the core 272. A concentric annular depending wall 282 is provided on the flip top 254 spaced radially outward from core 272. The annular depending wall includes a positive closure locking bead 284 which is adapted to receive and engage the complementary bead 286 provided at the mouth of the neck portion 276. When the cap is closed as shown in FIGS. 17 and 18, the bead 284 snaps into position beneath the bead 286 for holding the cap in a closed position and sealing against leakage. The double bead seal 284, 286 provides the primary fluid seal of the cap. The wiper/blade 292 is the secondary seal.

In the preferred embodiment, a recess channel 288 is provided about the perimeter of the neck portion 276 to provide for clearance between the tab 284 and the cap body 260 to assure that tolerances, excess fluid or other contaminants do not preclude proper closure of the cap.

In the preferred embodiment of the invention, the highly polished conical tip 274 terminates at a point 290 at the center of the open neck portion of the cap. An annular wiper rim or blade 292 extends inwardly from the inner peripheral side wall of the neck 276 and engages the edge 294 at or just below the intersection of the cone conical surface and cylindrical surface (see FIG. 19). This assures that any fluids which may be located by the formation of a meniscus at the intersection of the flip top and the neck are broken when the top is opened, the blade 292 wiping or braking the seal of the meniscus, causing the excess fluids to drop back down into the bottle. This reduces evaporation which occurs when the bottle is opened and assures that as much of the fluid is retained for usable function as possible during use of the reagent pack.

While the bottle cap of the subject invention is adapted to stay open by use of the over center spring defined by the bracket 258 and the live hinge 256, an alternative retainer is provided, as shown in FIGS. 10, 15 and 16. Specifically, the reagent pack 40 may be provided with a plurality of apertures in the bottle carrier thereof as at 300 and 302, on opposite sides of the center bottle opening (see FIGS. 10 and 16). Retainer posts 304 are adapted to be disposed in and snugly fit within the apertures 300 and 302, and include enlarged heads 306. Where desired, the flip top portion of the cap, when opened, is designed to be engaged by one or more of the posts 304, whereby the cap may be retained in the open position, irrespective of the use of the over center live hinge spring arrangement shown. In the preferred embodiment, center bottle engages the two adjacent posts 304, whereas a single post 304 is sufficient to maintain the outboard bottles 34, 38 in an open condition.

While certain features and embodiments of the invention have been described in detail herein, it will be understood that the invention includes all enhancements and modifications within the scope and spirit of the following claims.

What is claimed is:

1. A reagent pack utilized in a reagent pack receiving bucket of a carousel of an immunoassay apparatus wherein the carousel is configured to receive and positively retain multiple reaction cells and at least one reagent pack and the bucket is circular and located between a center spindle and reaction cell receiving wells, said reagent pack comprising:

an arcuate, free standing, vertical support framework comprising carousel engaging means configured to engage a cooperating means on the carousel and releasably secure the pack to the carousel;

a vertical ridge extending radially inwardly from said support framework and terminating in an inclined surface, said ridge positively engaging a positioning slot and locking elements within said carousel bucket for accurately aligning and locking said framework within said bucket;

a support surface attached to and extending outwardly from said framework; and a plurality of visible reagent containers releasably secured to and carried by said support surface, said support surface comprising means for accurately positioning the reagent containers relative to the framework.

2. The reagent pack of claim 1 wherein the arcuate support framework encompasses an included angle of not more than 120°.

3. The reagent pack of claim 1 wherein each of the plurality of reagent containers comprises a cylindrical bottle having an open top and a closable cap associated therewith and a closed bottom and wherein the support surface includes support means for supporting said bottles at an angle wherein a longitudinal axis of the bottle is offset from a vertical axis when the reagent pack is releasably secured in the immunoassay apparatus carousel.

4. The reagent pack of claim 3 wherein the reagent pack further comprises a means for selectively maintaining the cap associated with each of the bottles in an open position.

5. The reagent pack of claim 3, wherein the framework further comprises visible locator means to visibly locate and ensure proper alignment of the reagent pack when said reagent pack is releasably secured to the immunoassay apparatus carousel.

* * * * *